US008382748B2

(12) United States Patent
Geisel

(10) Patent No.: US 8,382,748 B2
(45) Date of Patent: *Feb. 26, 2013

(54) HIGH EFFICIENCY, PRECISION ELECTROSURGICAL APPARATUS AND METHOD

(76) Inventor: Donald J. Geisel, Clifton Park, NY (US)

( * ) Notice: Subject to any disclaimer, the term of this patent is extended or adjusted under 35 U.S.C. 154(b) by 1166 days.

This patent is subject to a terminal disclaimer.

(21) Appl. No.: 12/023,562

(22) Filed: Jan. 31, 2008

(65) Prior Publication Data

US 2008/0119841 A1 May 22, 2008

Related U.S. Application Data

(63) Continuation-in-part of application No. 11/552,581, filed on Oct. 25, 2006, now Pat. No. 7,922,713.

(60) Provisional application No. 60/755,900, filed on Jan. 3, 2006.

(51) Int. Cl.
*A61B 18/04* (2006.01)
*A61B 18/14* (2006.01)

(52) U.S. Cl. .................. 606/29; 606/37; 606/45; 606/49

(58) Field of Classification Search .................... 606/29, 606/34, 37–40, 45–49
See application file for complete search history.

(56) References Cited

U.S. PATENT DOCUMENTS

| 4,196,734 | A | | 4/1980 | Harris |
| 5,046,506 | A | * | 9/1991 | Singer .......................... 600/554 |
| 5,807,392 | A | | 9/1998 | Eggers |
| 5,885,277 | A | * | 3/1999 | Korth .............................. 606/35 |
| 7,922,713 | B2 | * | 4/2011 | Geisel ............................ 606/29 |
| 2005/0096681 | A1 | * | 5/2005 | Desinger et al. ............. 606/169 |
| 2009/0024154 | A1 | * | 1/2009 | Williams et al. ............... 606/32 |

* cited by examiner

*Primary Examiner* — Lee Cohen
(74) *Attorney, Agent, or Firm* — Schmeiser, Olsen & Watts, LLP

(57) ABSTRACT

A method and associated electrosurgical apparatus for cutting and/or coagulating living tissue of a mammal. The glow blade cuts and/or coagulates the tissue with a glow blade accompanied by sufficient electrical current across the tissue to enable the cutting and/or coagulating to be performed while the glow blade is heated to a sufficient temperature. The electrosurgical apparatus includes the glow blade, a radio frequency (RF) generator such that a first output of the RF generator is electrically connected to the glow blade, and an energy source coupled to the glow blade. The RF generator is configured to supply sufficient RF power and associated electrical current across the living tissue for performing the cutting and/or coagulating by the glow blade while sufficient energy is being supplied by the energy source to heat the glow blade to a sufficient temperature for performing the cutting and/or coagulating by the glow blade.

26 Claims, 12 Drawing Sheets

US 8,382,748 B2

HIGH EFFICIENCY, PRECISION ELECTROSURGICAL APPARATUS AND METHOD

RELATED APPLICATION

The present patent application is a continuation-in-part of U.S. patent application Ser. No. 11/552,581, filed Oct. 25, 2006, now U.S. Pat. No. 7,922,713, and entitled "HIGH EFFICIENCY, PRECISION ELECTROSURGICAL APPARATUS AND METHOD" and is incorporated herein by reference in its entirety, wherein U.S. patent application Ser. No. 11/552,581 claims priority to U.S. Provisional Application No. 60/755,900, filed Jan. 3, 2006 and entitled "HIGH EFFICIENCY, PRECISION ELECTROSURGICAL APPARATUS AND METHOD".

FIELD OF THE INVENTION

The present invention relates to an electrosurgical apparatus for cutting and/or coagulating living tissue, a method of forming the electrosurgical apparatus, and methods of using the electrosurgical apparatus.

BACKGROUND OF THE INVENTION

Conventional electrosurgical devices are widely employed by surgeons for cutting and/or coagulating human tissue in operating rooms. They are used in lieu of a conventional blade or knife in situations where bleeding tissue can cause unwanted loss of blood. The basic electrosurgical device consists of a intermediate frequency RF generator with power capability on the order of several hundred watts, driven by approximately 1000 volts or higher. The generator common is connected to a patient pad, upon which a patient lies. The hot lead of the generator is connected via an insulating cable to a conductive shaped end for tissue cutting, called the cutting probe. The shape, for example, could be needle like, circular or flat. It is this conductive end which is employed for tissue cutting. When the conductive end of the generator hot lead is placed in contact with the patent, current flows through the patient to the patient pad. Since the current density is extremely high at the cutting probe, tissue is cut by burning and vaporization.

As tissue is cut, substantial smoke is generated with carbon and debris collecting on the cutting probe and along the cutting path through tissue. The destroyed tissue suffers trauma and healing is prolonged and accompanied by internal scaring. The currents from the generator must always flow from the cutting probe through the patient. Depending on the region of cutting, unwanted currents will flow via the path of least resistance to the patient pad. These currents could flow through sensitive organs, causing irreparable damage. High voltage is essential for the conventional electrosurgical unit to function. This level of energy is hazardous to both patient and surgeon. The precision of cutting by an electrosurgical approach does not compare with a conventional blade because a substantial amount of tissue is actually destroyed during cutting.

With the conventional electrosurgical unit, high voltage is necessary to initiate and maintain a current path from the cutting probe to target tissue, which is a form of ionization at room temperatures and pressure.

Moreover, it is stated in the Internet website whose address is a concateneation of "http://" and "www.usaccc.org/research/Hemostasis.jsp" that "[e]ighty to ninety percent of combat-related deaths occur within 1 hour of wounding. Fifty percent or more are attributable to uncontrolled bleeding. Recent evidence suggests that the majority of deaths due to hemorrhage in potentially survivable casualties involved non-compressible hemorrhages or were areas not conducive to a tourniquet. Currently, there is no ability to control non-compressible hemorrhage in casualties with clotting deficiencies short of immediate surgery."

Thus, there is a need for an electrosurgical device that overcomes at least one of the aforementioned disadvantages of conventional electrosurgical devices.

SUMMARY OF INVENTION

The present invention provides an electrosurgical apparatus for cutting and/or coagulating a local portion of living tissue of a mammal, said apparatus comprising:
  a glow blade;
  a radio frequency (RF) generator such that a first output of the RF generator is electrically connected to the glow blade; and
  an energy source coupled to the glow blade,
  wherein the RF generator is configured to supply sufficient RF power and associated electrical current across the living tissue for performing said cutting and/or coagulating by the glow blade while sufficient energy is being supplied by the energy source to heat the glow blade to a sufficient temperature for performing said cutting and/or coagulating by the glow blade.

The present invention provides a method for cutting and/or coagulating a local portion of living tissue of a mammal, said method comprising cutting and/or coagulating the local portion of the living tissue of a mammal with a glow blade accompanied by sufficient electrical current across the living tissue to enable said cutting and/or coagulating to be performed while the glow blade is heated to a sufficient temperature.

The present invention overcomes at least one of the disadvantages (identified supra) of conventional electrosurgical devices.

DETAILED DESCRIPTION OF THE INVENTION

Figure 1:
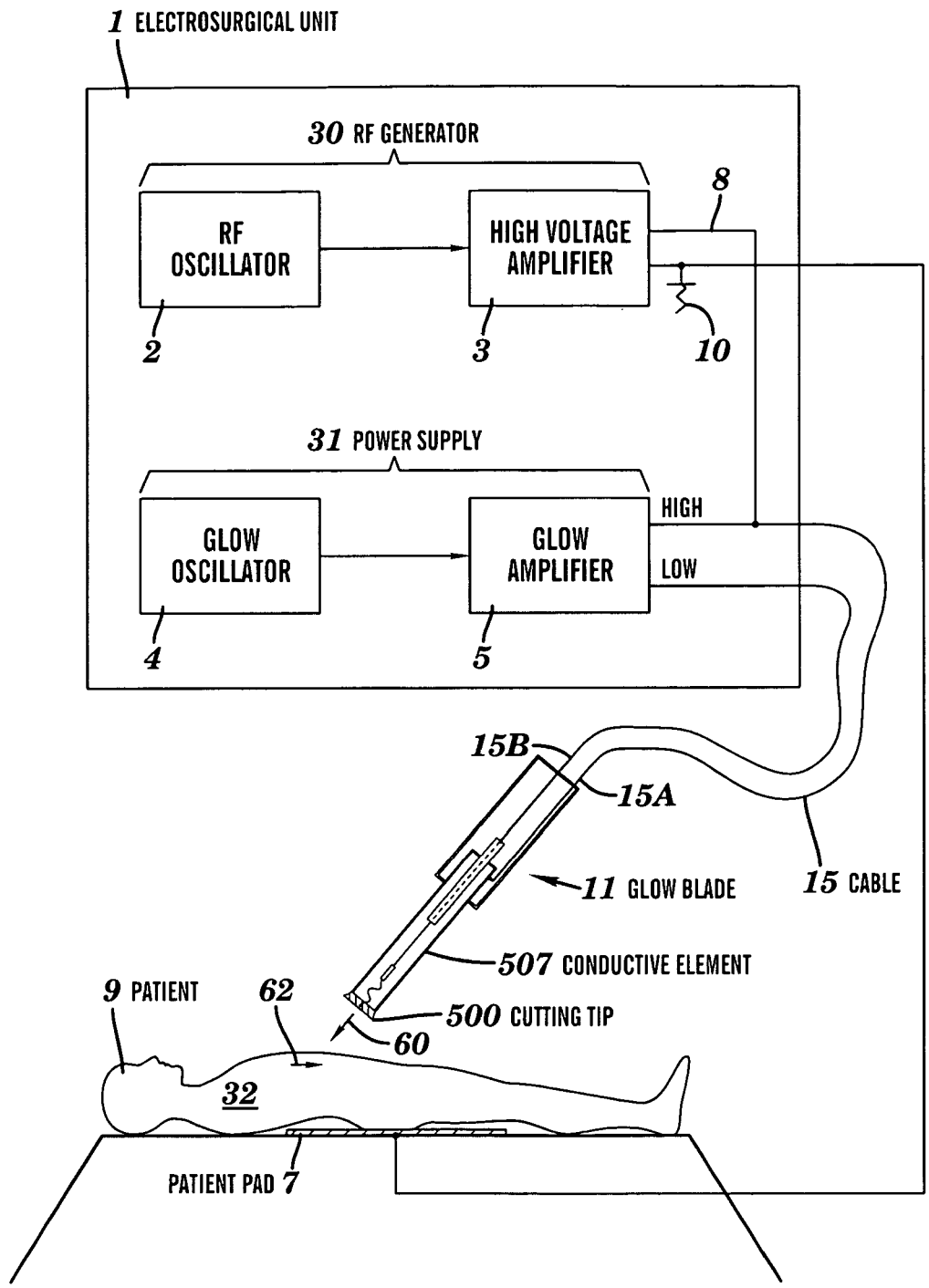
FIG. 1 depicts an electrosurgical apparatus in a monopolar (single ended) mode with a single glow blade for use with a patient, in accordance with embodiments of the present invention.

The present invention provides an electrosurgical apparatus having a glow blade for cutting and/or coagulating living tissue of a mammal. The phrase "cutting and/or coagulating" means cutting, coagulating, or both cutting and coagulating. The present invention teaches the advantages of a heated or glowing cutting blade for use in conjunction with an electrosurgical device. The cutting blade may be heated electrically or by other heating means (laser heating, ultrasonic heating, flame radiation, plasma etc.). Although specific embodiments of the present invention are described infra with respect to cutting and/or coagulating living tissue of a person or patient, the electrosurgical apparatus of the present invention may be employed generally for cutting and/or coagulating living tissue of a mammal. The mammal may be a human being such as, inter alia, a person in an operating room of a hospital or in a doctor's office, a soldier wounded in combat, etc. Alternatively, the mammal may be a non-human mammal (e.g., a rat, a dog, etc.).

The electrosurgical apparatus of the present invention provides advantages which include:

(1) a lower power electrosurgical unit for coagulating tissue as it cuts;

(2) reduced power cutting (up to 5 times lower than with conventional electrosurgical units);

(3) more precise and smooth cutting;

(4) less smoke form cutting;

(5) a cleaner cut;

(6) less patient trauma;

(7) faster healing;

(8) no carbon buildup on cutting blade;

(9) no carbon buildup on patient tissue;

(10) improved safety for patent and surgeon with lower voltage and power;

(11) even cutting at depth of blade;

(12) elimination of patient pad for dual glow blade approach;

(13) no sticking of cutting blade to tissue; and

(14) rapid coagulation of tissue which stops uncontrolled bleeding of soldiers wounded in combat.

Thus, the electrosurgical apparatus of the present invention discloses a substantial improvement over the conventional electrosurgical device. The improvement allows for cutting of tissue with accompanying coagulation, using reduced power and voltage, hence less current, yielding more precise cutting, less tissue trauma, faster healing, and improved safety for patient and surgeon. Moreover, the electrosurgical apparatus of the present invention may be used for rapid coagulation of tissue (with or without accompanying cutting) in order to stop bleeding immediately (e.g.; to stop uncontrolled bleeding of soldiers wounded in combat). This rapid coagulation has not been previously practical in a battery powered field unit. With the present invention, however, a battery-powered unit is now practical.

The present invention provides an electrosurgical apparatus for coagulating living tissue. The electrosurgical apparatus comprises a glow blade, a radio frequency (RF) generator, and one or two loop power supplies. The glow blade has one or two glow loops, each glow loop being a loop of resistance wire. The RF generator supplies RF energy for coagulating living tissue by the glow blade. The one or two loop power supplies respectively correspond to the one or two glow loops, each loop power supply adapted to independently supply sufficient electrical current to its respective glow loop to heat the resistance wire of its respective glow loop to a glow such that the glow loop is ready and able to give off electrons to enable the one or two glow loops to coagulate the living tissue. The RF generator and the one or two loop power supplies are configured to operate concurrently, while the one or two glow loops are heated to a glow, to supply both sufficient RF power and associated electrical current across the living tissue for coagulating the living tissue by the one or two glow loops. A first output of the RF generator is electrically coupled to the one or two glow loops.

A first power supply of the one or two power supplies is configured such that there is no electrical current path from any output of the RF generator into the first power supply.

In alternative glow blade embodiments, the glow blade may be a single glow blade or a dual glow blade. The dual glow blade comprises two conductive elements such that one or both conductive elements may be heated for cutting and coagulating the living tissue.

The sections entitled "Single or Monopolar Glow Blade Embodiment" and "Dual or Bipolar Glow Blade Embodiment" will describe infra embodiments illustrated in FIGS. 1-11 in which the energy source is one or two power supplies. However, the scope of the present invention includes any alternative energy source that may be used to heat the glow blade. Accordingly, all features of the present invention described in conjunction with FIGS. 1-11 are applicable to any alternative energy source, except those features that physically and/or logically require the existence of one or two power supplies as the energy source for heating the glow blade. The section entitled "Alternative Energy Sources", described infra in conjunction with FIGS. 12-13, will describe the electrosurgical apparatus of the present invention with use of alternative energy sources.

Single or Monopolar Glow Blade Embodiment

FIG. 1 depicts an electrosurgical apparatus in a monopolar mode with a single glow blade for use with a patient, in accordance with embodiments of the present invention. The electrosurgical unit apparatus of FIG. 1 may be powered by alternating current (AC) power, direct current (DC) power such via batteries (e.g., isolated rechargeable batteries), or by a combination of AC power and DC power.

Figure 8:
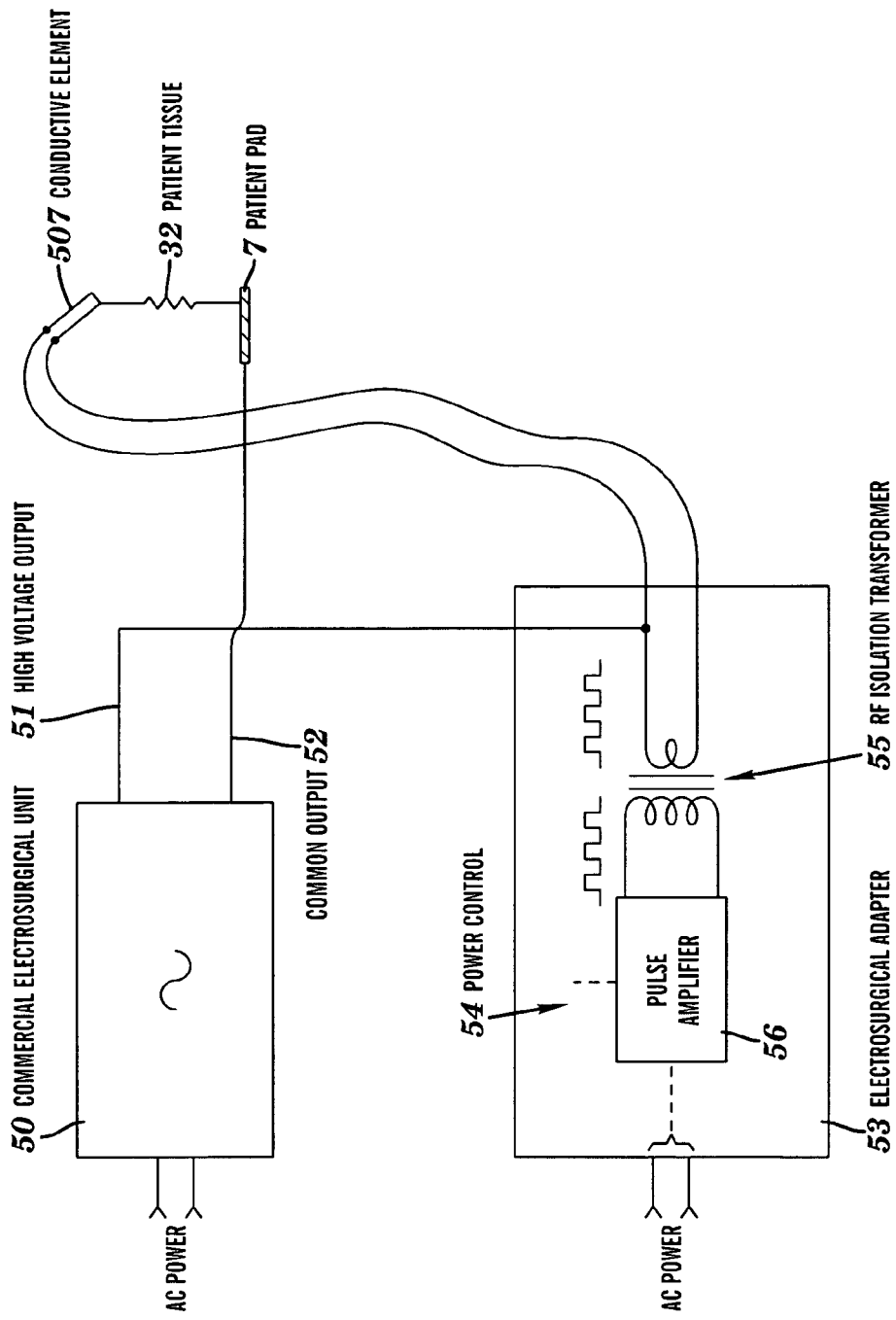
FIG. 8 depicts an alternative electrosurgical apparatus in a monopolar mode with a single glow blade for use with a patient, in accordance with embodiments of the present invention.

The electrosurgical apparatus of FIG. 1 comprises an electrosurgical unit 1 and a glow blade 11, which may be contained within a single enclosure as shown in FIG. 1 or may be provided in separate enclosures as depicted in FIG. 8 described infra. The electrosurgical unit 1, which comprises a radio frequency (RF) generator 30 and a power supply 31, is electrically connected to the glow blade 11 by cable 15 which comprises conductors 15A and 15B. The power supply 31 is configured such that there is no electrical current path from any output of the RF generator into the power supply 31.

The glow blade 11 comprises a glow loop 6 which functions as a cutting probe that maintains an arc, wherein the arc cuts the target tissue. The glow loop 6 is a loop of resistance wire heated to a glow (e.g., a cherry red color) by electrical current. The glowing of the glow loop 6 may be analogous to a filament in a vacuum tube that is heated to promote electron emission from "filament to plate" or "cathode to plate" elements of the vacuum tube. Thus, it should be understood that the glow loop 6 is ready and able to give off electrons.

The conductive element 507 is electrically connected to the hot lead 8 of the RF generator 30. The conductive element 507 is RF excited such that a cutting tip 500 of the conductive element 507 cuts a local portion of tissue 32 of a patient 9. The tissue 32 is living tissue. The RF generator 30 supplies the cutting energy and also causes RF heating of the tissue 32. As the tissue 32 is cut, coagulation of tissue results from the RF heating, which immediately stops bleeding.

Figure 7:
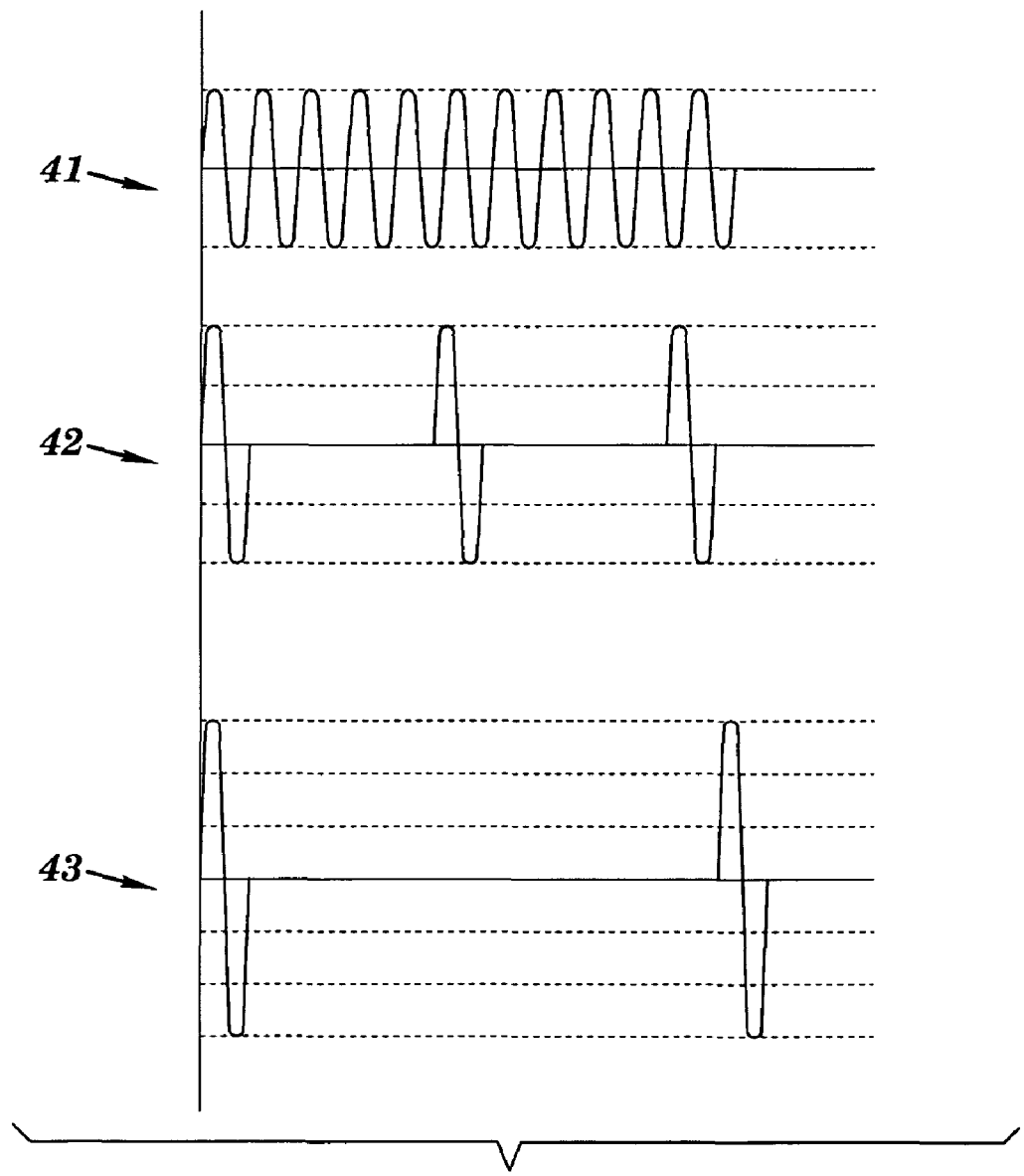
FIG. 7 depicts examples of radio frequency (RF) generator output wave shapes, in accordance with embodiments of the present invention.

The RF generator 30, which supplies RF energy for tissue cutting, comprises a RF oscillator 2 and a high voltage (HV) amplifier 3, wherein the RF oscillator 2 drives the high voltage amplifier 3. In one embodiment, the RF oscillator 2 has an operating frequency between 100 KHz and 10 MHz (e.g., 500 KHz). The high voltage amplifier 3 may generate variable wave shapes, including modulated types. For example, FIG. 7 depicts examples of radio frequency (RF) generator output wave shapes, in accordance with embodiments of the present invention. In FIG. 7, a continuous wave (i.e., 100% duty cycle) is shown in wave shape 41 with amplitude of 100 volts RMS. A modulated shape of approximately 30% duty cycle is shown at wave shape 42 with higher amplitude than wave shape 41. The duty cycle of the modulated shape is defined as the ratio of the pulse duration in each cycle to the cycle period. A modulated shape of approximately 10% duty cycle is shown at wave shape 43, with much higher amplitude than wave shape 41. Different wave shapes may be employed for different procedures (e.g., cutting with accompanying coagulation; coagulation without accompanying cutting; etc; etc.). For example, modulated pulse shapes having duty cycles from about 20% to about 100%, which include the wave shapes 41 and 42 of FIG. 7, may be employed for cutting with accompanying coagulation. As another example, modulated pulse shapes having duty cycles from about 2% to about 20%, which include the wave shape 43 of FIG. 7, may be employed for coagulation with or without accompanying cutting, which defines an "enhanced coagulation" mode of operation. Since wave shape 43 may contain complex wave patterns, an alternate method to describe wave shape 43 is by a crest factor defined as a ratio of peak voltage to rms voltage, wherein values of the crest factor may range from about 5 to about 10 with peak voltages up to several thousand volts. Moreover, wave shape 41 may be alternatively employed for pure cutting without accompanying coagulation, which defines a "pure cutting" mode of operation. A feature of the glow blade is that cutting with coagulation of highly vascular tissue can be achieved in an enhanced coagulation mode such as wave shape 43. Conventional devices cannot cut a liver in any mode and achieve coagulation. The glow blade does not stick to the target tissue in the enhanced coagulation mode. This makes the enhanced coagulation mode of the present invention especially useful for concurrent cutting with coagulation, or for coagulation alone following an alternative cutting process that does not utilize the glow blade of the present invention.

The wave shape 43 is an example of an "enhanced coagulation waveform" which is defined as a waveform having a duty cycle from about 2% to about 20% and/or having a crest factor from about 5 to about 10.

The variable wave shapes have an associated time-averaged output that may be varied from 50 to 500 volts (e.g., a sine wave with 100 volts RMS output voltage). Successful tissue cutting will occur, inter alia, with 100 volts while consuming only 5 watts of power, which implies a power range of 1.25 to 125 watts for the output voltage range of 50 to 500 volts. The lower output voltage of the RF generator 30, as compared the much higher output voltage of at least 1000 volts of a conventional electrosurgical device, results in lower current through the target tissue and bulk of the patient 9.

The power supply 31 comprises a glow oscillator 4 and glow amplifier 5, wherein the glow oscillator 4 drives the glow amplifier 5. The output of the glow amplifier 5 is a low-voltage, high-current signal to heat up the conductive element 507 of the glow blade 11. By adjusting the duty cycle of the glow oscillator 4, one can adjust the temperature of conductive element 507. The glow components (i.e., the glow oscillator 4 and the glow amplifier 5) are like a variable battery connected across a light bulb. The glow oscillator 4 and glow amplifier 5 could be replaced by any suitable adjustable power source. In one embodiment, the power supply 31 is a DC source (e.g., one or more batteries) that drives a pulse amplifier to generate a pulse train that is sent to the conductive element 507. The power of the pulse train from the power supply 31 controls the temperature of the conductive element 507. The power of the pulse train from the power supply 31 may be varied by adjustment of the pulse amplitude, duty cycle and/or the pulse frequency. In one embodiment, the power source for the power supply 31 is an AC power source such as 115 VAC mains (e.g., the electrosurgical adapter 53 of FIG. 8, described infra).

The RF generator 30 is electrically coupled to the power supply 31. The hot lead 8 of the high voltage amplifier 3 is electrically connected to both the output high side of the glow amplifier 5 and a first portion of the conductive element 507 via conductor 15A. The output low side of glow amplifier 5 is electrically connected to a remaining portion of the conductive element 507 via conductor 15B. Those skilled in the art realize that the outputs of supply 31 are reversible; i.e., high can be swapped with low and vice versa. The circuit ground 10 of the high voltage amplifier 3 is electrically connected to patient pad 7 which is in physical and electrical contact with the patient 9 such as, inter alia, the patient 9 lying or sitting on the pad 7. Generally, the pad 7 is an electrically conducting element that can be positioned in physical and electrical contact with any portion of the patient 9, such as, inter alia, underneath the patient 9 in contact with the patient's back and/or buttock as in FIG. 1, on or around an arm or leg of the patient 9, on the chest of the patient 9, etc. The hot lead 8 output (via circuit ground 10) of the RF generator 30 is electrically connected to the pad 7 to facilitate an electric current flowing through the tissue of the patient 9 between the conductive element 507 and the pad 7. The circuit ground 10 is actually a return path for the hot lead 8 output and is sometimes called ground or minus terminal, where such ground is sometimes used as a convenience designation and does not necessarily imply any connection to earth ground. For example the RF generator 30 may incorporate an output transformer where it is common practice to float output common from earth ground for safety reasons.

When the conductive element 507 touches the patient 9, RF current flows from conductive element 507 through the target tissue, through the bulk of the patient 9, and to the patient pad 7. The cutting of the tissue 32 occurs at the points of contact between the cutting tip 500 of the conductive element 507 and the patient 9. As the conductive element 507 is moved into the tissue in a direction 60, tissue of the patient 9 is cut.

Figure 5:
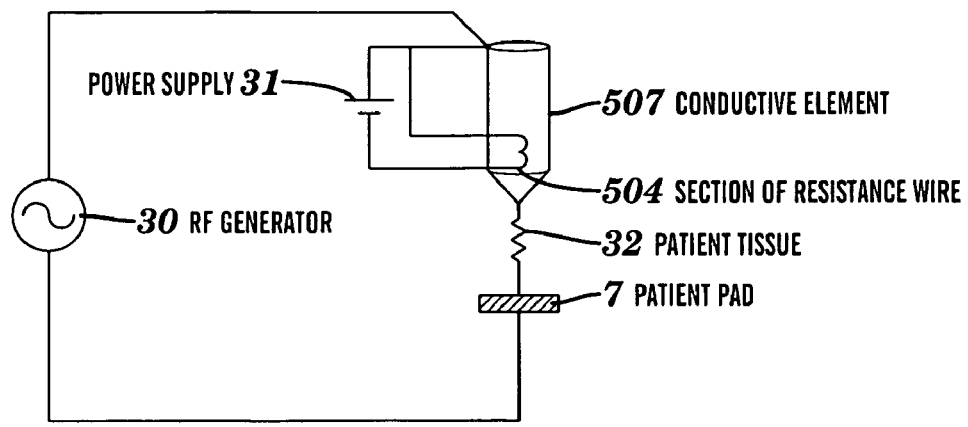
FIG. 5 depicts an equivalent electric circuit representing the electrosurgical apparatus and patient of FIG. 1, in accordance with embodiments of the present invention.

FIG. 5 depicts an equivalent electric circuit representing the electrosurgical apparatus and patient of FIG. 1, in accordance with embodiments of the present invention. In FIG. 5, the RF generator 30 connects to conductive element 507. The power supply 31 is shown simplistically as a battery and connects across the section of resistance wire 504. The conductive element 507 is shown in electrical contact with patient tissue 32, indicated as a resistive element. A portion of this resistive element adjacent to the patient pad 7 is the remainder of the patient which touches the patient pad 7. The patient pad 7 is electrically connected back to the RF generator 30 common at circuit ground 10. The battery heats up the section of resistance wire 504 and RF power is connected to the conductive element 507 which in turn transports energy to cut the tissue 32 of the patient 9. The RF current path is from the RF generator 30 to the conductive element 507, through the tissue being cut, through the bulk of the patient, to the pad 7 and back to the RF generator 30. The battery current path is through the section of resistance wire 504, so as to facilitate the transport of RF energy to the target tissue 32. The RF current through the patient tissue 32 achieves the cutting of the tissue 32 of the patient 9. Because the applied RF voltage is substantially lower than the voltage of the conventional electrosurgical devices, lower and safer current flows through the patient as a result of usage of the single glow blade electrosurgical apparatus of the current invention.

Figure 3:
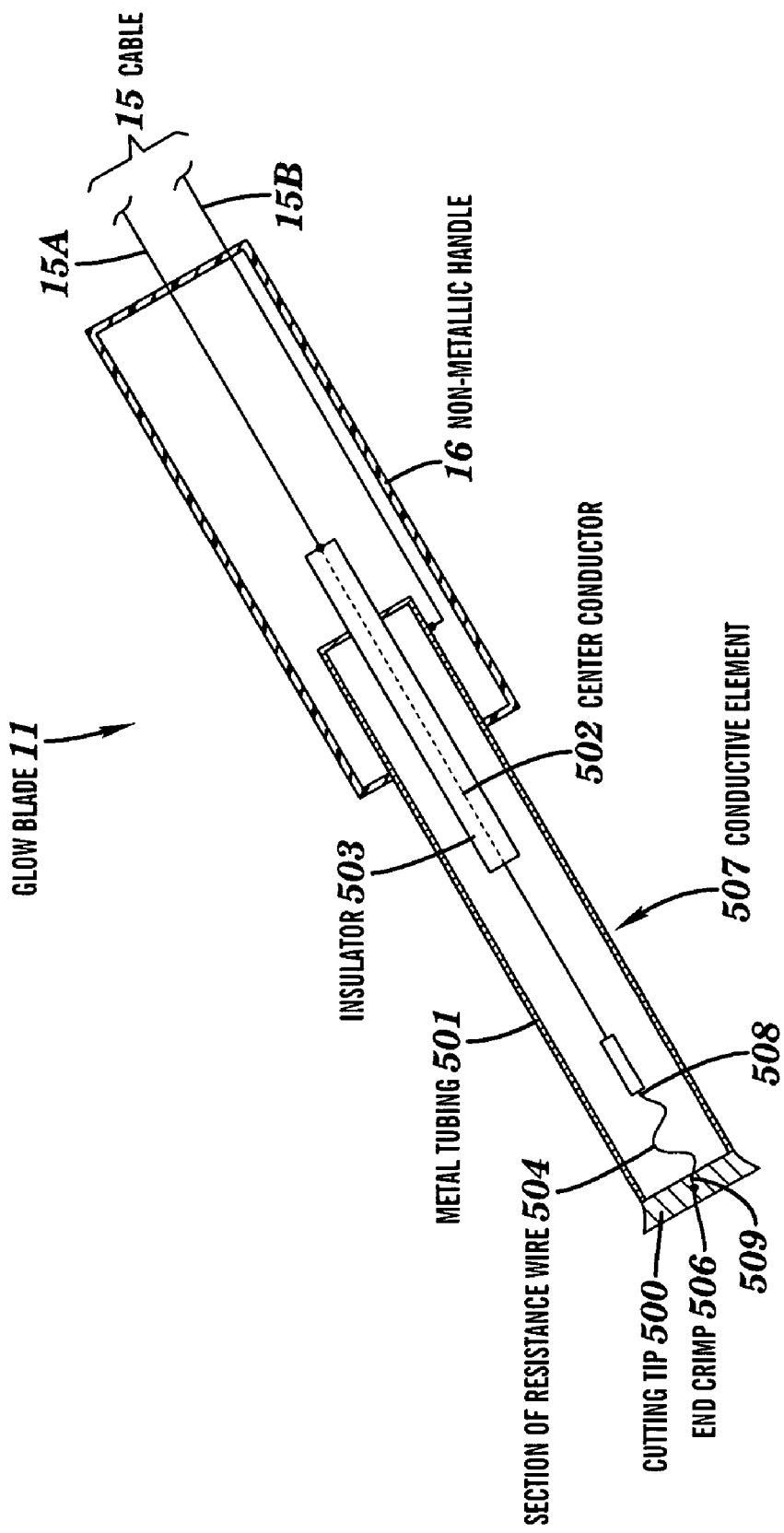
FIG. 3 depicts the single glow blade of FIG. 1 in greater detail, in accordance with embodiments of the present invention.

FIG. 3 depicts the single glow blade 11 of FIG. 1 in greater detail, in accordance with embodiments of the present invention. Cable 15 simultaneously provides both RF and glow power to conductive element 507 from RF generator 30 and glow amplifier 5, respectively. A non-metallic handle 16 supports the conductive element 507 and is mechanically fastened to conductive element 507. The heated portion of the conductive element 507 near the cutting tip 500 comprises resistance wire 504 in the form any functional geometry, protected by an enclosure of metal tubing 501. For example, the resistance wire 504 may have the shape of a straight or curved wire or may represent a bulk electrically resistive material. The heated portion of the conductive element 507 is near the cutting tip 500 of conductive element 507 where most efficient cutting occurs. In one embodiment, the cutting tip 500 has a flat surface configured to contact tissue. Heating power is supplied by cable 15A via center conductor 502, which is surrounded by insulator 503 and lies within the metallic tubing 501 (e.g., along the center line of the metallic tubing 501). The center conductor 502 may comprise copper, but may alternatively comprise any other suitable electrically conductive metal or metallic alloy (e.g., nickel, chrome, stainless steel, etc.). Center conductor 502 supplies power to an end 508 of a section of resistance wire 504 which conducts heat to the cutting tip 500. Another end 509 of the section of resistance wire 504 is electrically connected to the metallic tubing 501 by end crimp 506. The metallic tubing 501 is connected to cable 15B as shown. Thus, the current path from cable 15A is down the center conductor 502, through the section of resistance wire 504 and back along the outside of metallic tubing 501 to cable 15B. Current causes the section of resistance wire 504 to heat up and thus the cutting tip 500 becomes hot and may glow. The metal tubing 501 mechanically protects the section of resistance wire 504. The metal tubing 501 could be eliminated and the section of resistance wire 504 could function as the cutting element and assume numerous shapes such as a narrow or circular single loop or multiple loops.

FIG. 8 depicts an alternative electrosurgical apparatus in a single ended (i.e., monopolar) mode with a single glow blade for use with the patient 9 of FIG. 1, in accordance with embodiments of the present invention. The electrosurgical apparatus of FIG. 8 differs from the electrosurgical apparatus of FIGS. 1 and 5 in that: a commercial electrosurgical unit 50 of FIG. 8 replaces the RF generator 30 of FIGS. 1 and 5; and the electrosurgical adapter 53 of FIG. 8 replaces the power supply 31 of FIGS. 1 and 5. In all other respects, the electrosurgical apparatus of FIG. 8 and the electrosurgical apparatus of FIGS. 1 and 5 are essentially the same electrosurgical apparatus with respect to structure and functionality.

The commercial electrosurgical unit 50 is the RF power portion of a conventional electrosurgical apparatus used in the prior art. The glow blade 11 (see FIG. 1) comprises the conductive element 507 and operates in conjunction with the electrosurgical adapter 53. The commercial electrosurgical unit 50 receives AC power as shown and has a high voltage output 51 and a common output 52 connected to RF circuit ground. The high voltage output 51 is electrically connected, via the electrosurgical adapter 53, to conductive element 507 which contacts the patient tissue 32. The common output 52 is electrically tied to the patient pad 7. The electrosurgical adapter 53, which converts AC power to a pulse train to provide power to the conductive element 507, comprises a pulse generator/amplifier 56 and a RF isolation transformer 55. An operator power control 54 connects to the pulse generator/amplifier 56 and controls the power in the pulse train by varying pulse rate, duty cycle, or amplitude of the pulse train, which controls the temperature of the conductive element 507. The RF isolation transformer 55 allows power to be coupled from the pulse amplifier 56 to the conductive element 507 while providing a high impedance for any stray RF current flowing from the electrosurgical unit 50. The transformer 55 is wound with sufficient distance between primary and secondary coils to achieve the desired RF isolation and deliver the required power to be supplied to the conductive element 507. In one embodiment, the electrosurgical adapter 53 may be replaced by a battery such as a battery representing the power supply 31 of FIGS. 1 and 5, for use with the commercial electrosurgical unit 50.

The output from the electrosurgical adapter 53 of FIG. 8 is analogous to the output from the power supply 31 of FIG. 1. In FIG. 1, the output of the power supply 31 is electrically decoupled from the AC power source of the RF generator 30 (e.g., by use of a battery as a power source of the power supply 31), which prevents unwanted RF power from flowing from the RF generator 30 to the power source of the power supply 31. Similarly in FIG. 8, the output of the electrosurgical adapter 53 is electrically decoupled from its AC power source and hence the power source of the electrosurgical unit 50 due to the output of the electrosurgical adapter 53 being decoupled by the RF isolation transformer 55, which prevents unwanted RF power from flowing from the electrosurgical adapter 53 to the power source of the electrosurgical adapter 53.

The single glow blade may be used for rapid coagulation of tissue (without accompanying cutting of tissue) in order to stop bleeding immediately (e.g.; to stops uncontrolled bleeding of soldiers wounded in combat). In one embodiment for such coagulation applications, the conductive element 507 may be may be brushed along the surface of the tissue being coagulated (e.g., moved in a brushing-type motion in a direction that is about parallel to the surface of the tissue being coagulated, with actual contact or with a small gap; e.g., about in the direction 62 in FIG. 1). In one embodiment, successful coagulation of tissue (without accompanying cutting of tissue) will occur with output power from the RF generator in a range of 1.25 to 125 watts.

Thus the RF generator 30 and the power supply 31 are configured to operate concurrently, while the conductive element 507 is heated to a glow, to supply both sufficient RF power and associated electrical current across the living tissue 32 for cutting and/or coagulating the living tissue 32 by the conductive element 507.

The inventor of the present invention has determined that the single glow blade embodiment of the present invention may be beneficially employed in a non-glowing mode for the conductive element, as an improvement over conventional electrosurgical devices of the prior art, if the single glow blade embodiment is implemented as described supra except that the conductive element 507 performs cutting and/or coagulation of tissue at a temperature below the minimum glow temperature of the material of the conductive element 507 (e.g., at a temperature in a range of about 300° F. to just below the minimum glow temperature). The minimum glow temperature of the material is defined as the minimum temperature at which the material glows (i.e., emits electromagnetic radiation in the visible portion of the electromagnetic spectrum).

Dual or Bipolar Glow Blade Embodiment

The bipolar glow blade embodiment provides an alternative mode of operation that totally eliminates the patient pad of the single glow blade and eliminates associated currents which would otherwise travel through the patient's body. Two heated elements, or one heated element and one non-heated element, are placed, side by side, nearly touching each other and one or both made to glow. In this scenario, the RF generator is connected across the two elements. The heated elements are resistive elements. When the elements touch the patient's tissue, current flows from one element to the other element via the tissue that contacts the tip of the elements. If this approach were attempted with a conventional electrosurgical technology in a blend or coagulation mode using unheated elements, the required higher voltage would arc and short one element to the other due to carbon and tissue debris between the elements. With the bipolar glow blade and lower voltage plus constant glowing of one or both elements to burn away debris, arcing is eliminated. Tissue cutting with this bipolar glow blade is practical and eliminates the patient pad and undesirable body currents. As with a single element, cutting is achieved along with coagulation of tissue, wherein the coagulation reduces or eliminates loss of blood.

Figure 2:
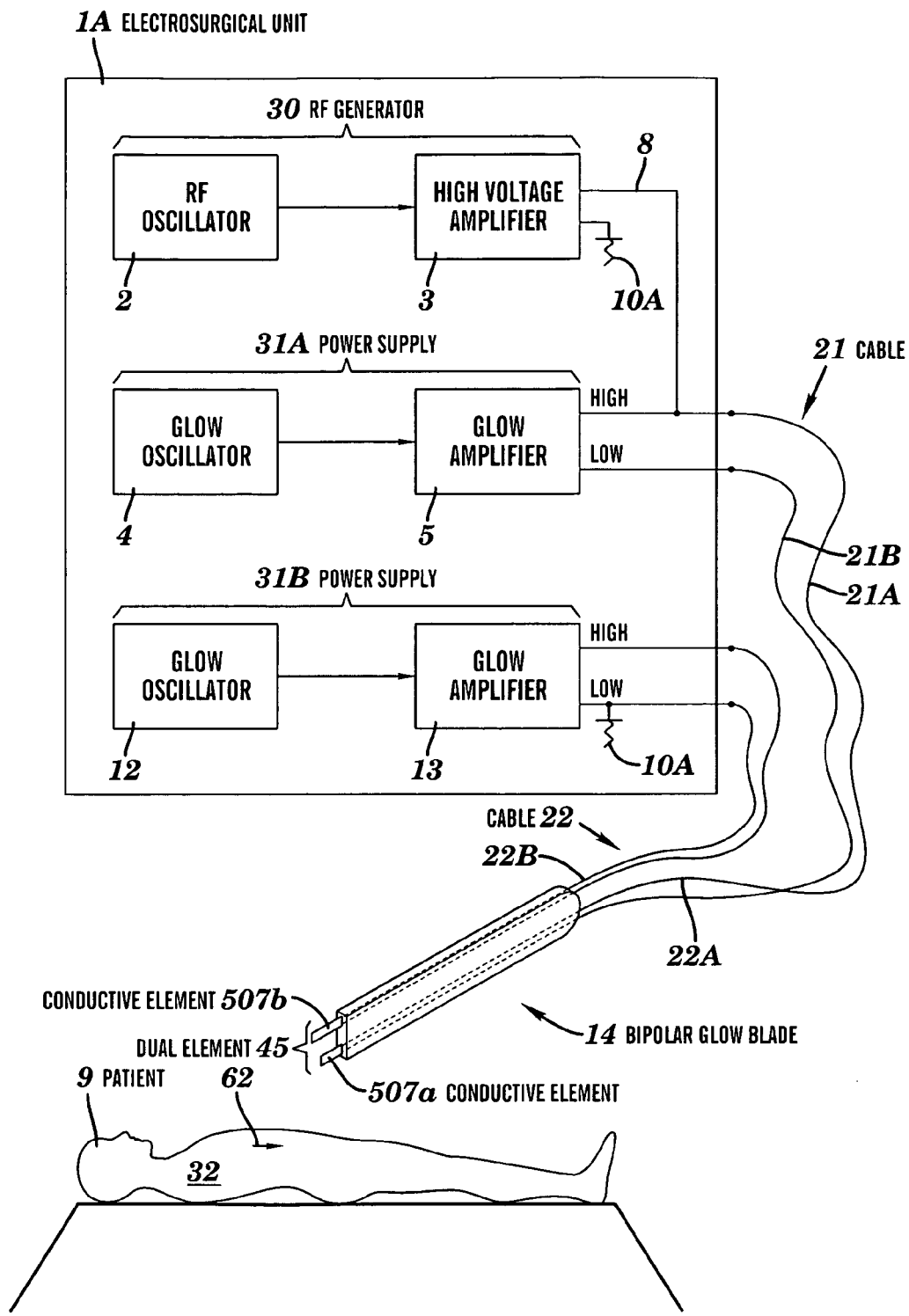
FIG. 2 depicts an electrosurgical apparatus configured for bipolar (differential) operation with a dual glow blade for use with a patient, in accordance with embodiments of the present invention.

FIG. 2 depicts an electrosurgical apparatus configured for bipolar operation with a bipolar glow blade for use with a patient, in accordance with embodiments of the present invention. The electrosurgical unit apparatus of FIG. 2 may be powered by alternating current (AC) power, direct current (DC) power such via batteries (e.g., isolated rechargeable batteries), or by a combination of AC power and DC power.

Figure 9:
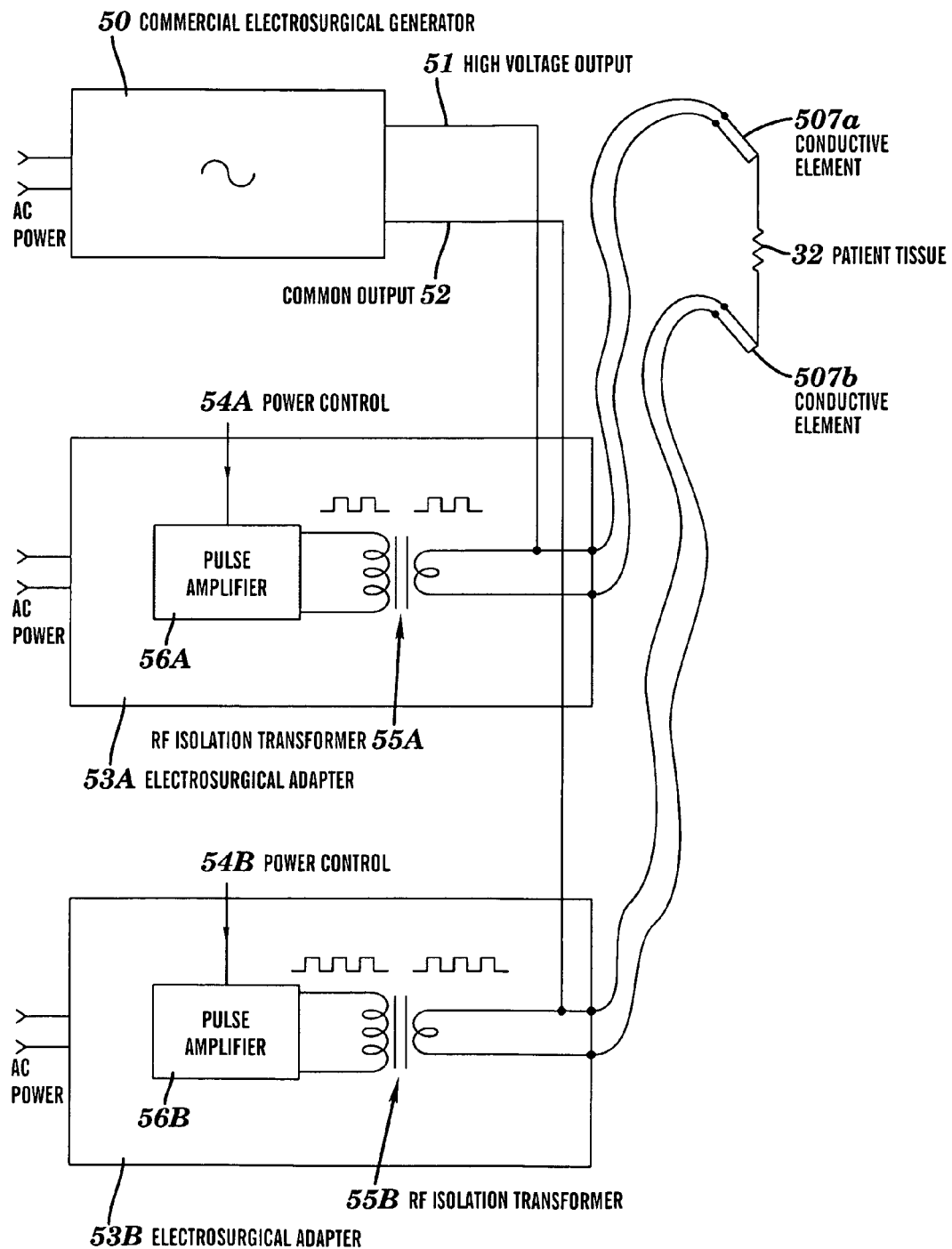
FIG. 9 depicts an alternative electrosurgical apparatus configured for bipolar operation with a dual glow blade for use with a patient, in accordance with embodiments of the present invention.

The electrosurgical apparatus of FIG. 2 comprises an electrosurgical unit 1A and a bipolar glow blade 14, which may combined in a single enclosure as shown in FIG. 2 or may be provided in separate enclosures as depicted in FIG. 9 described infra. The electrosurgical unit 1A, which comprises a radio frequency (RF) generator 30, a power supply 31A, and a power supply 31B, is electrically connected to the bipolar glow blade 14 by cable 21 and cable 22, respectively. The power supply 31A is analogous to the power supply 31 of FIG. 1 and the power supply 31B is an added power supply which may be similar to, or identical with, the power supply 31A. Cable 21 comprises conductors 21A and 21B. Cable 22 comprises conductors 22A and 22B.

The power supply 31A is configured such that there is no electrical current path from any output of the RF generator into the power supply 31A.

The bipolar glow blade 14 comprises a dual element 45 comprising a conductive element 507a and a conductive element 507b. When used for cutting and/or coagulation, the conductive element 507a is heated and the conductive element 507b is either heated or non-heated. The bipolar glow blade 14 functions as a cutting probe that maintains an arc, wherein the arc cuts the target tissue. As compared to FIG. 1, the patient pad 7 has been eliminated in FIG. 2, and the RF cutting voltage appears from conductive element 507a (which is heated to a glow) to conductive element 507b (which is either heated or non-heated). When the conductive elements 507a and 507b of dual glow blade 14 come in contact with the patient tissue 32 (which is living tissue), cutting is achieved. As the tissue 32 is cut, coagulation of tissue results from the RF heating, which immediately stops bleeding.

Cable 21A and 21B supply both heating and RF power to conductive element 507a in a manner similar to the heating supplied by cables 15A and 15B to the conductive element 507 of FIG. 3. Cable 22A and 22B supply both heating power (if employed) and RF power return to element 507b in a manner similar to the heating supplied by cables 15A and 15B to the conductive element 507 of FIG. 3.

The bipolar glow blade 14 may have a metal tubing and non-metallic handle similar to the metal tubing 501 and the non-metallic handle 16 depicted for the single glow blade 11 in FIG. 3. The glow blade 14 may employ two assemblies similar to the glow blade 11 of FIG. 3, However, FIG. 2 shows the conductive elements 507a and 507b schematically as simple electrical loops.

The RF generator 30, which supplies RF energy for tissue cutting, comprises a RF oscillator 2 and a high voltage (HV) amplifier 3, wherein the RF oscillator 2 drives the high voltage amplifier 3. The RF oscillator 2 has an operating frequency between 100 KHz and 10 MHz (e.g., 500 KHz). The high voltage amplifier 3 generates variable wave shapes, including modulated types. The high voltage amplifier 3 generates variable wave shapes, including modulated types. For example, FIG. 7 depicts examples of radio frequency (RF) generator output wave shapes, in accordance with embodiments of the present invention. In FIG. 7, a continuous wave (i.e., 100% duty cycle) is shown in wave shape 41 with amplitude of 100 volts RMS. A modulated shape of approximately 30% duty cycle is shown at wave shape 42 with higher amplitude than wave shape 41. The duty cycle of the modulated shape is defined as the ratio of the pulse duration in each cycle to the cycle period. A modulated shape of approximately 10% duty cycle is shown at wave shape 43, with much higher amplitude than wave shape 41. Different wave shapes may be employed for different procedures (e.g., cutting with accompanying coagulation; coagulation without accompanying cutting; etc; etc.). For example, modulated pulse shapes having duty cycles from about 20% to about 100%, which include the wave shapes 41 and 42 of FIG. 7, may be employed for cutting with accompanying coagulation. As another example, modulated pulse shapes having duty cycles from about 2% to about 20%, which include the wave shape 43 of FIG. 7, may be employed for coagulation with or without accompanying cutting, which defines an "enhanced coagulation" mode of operation. Since wave shape 43 may contain complex wave patterns, an alternate method to describe wave shape 43 is by a crest factor defined as a ratio of peak voltage to rms voltage, wherein values of the crest factor may range from about 5 to about 10 with peak voltages up to several thousand volts. Moreover, wave shape 41 may be alternatively employed for pure cutting without accompanying coagulation, which defines the "pure cutting" mode of operation. A key feature of the glow blade is that cutting with coagulation of highly vascular tissue can be achieved in an enhanced coagulation mode such as wave shape 43. Conventional devices cannot cut a liver in any mode and achieve coagulation. The glow blade easily cuts live liver with coagulation and does not stick to the target tissue in the enhanced coagulation mode. This makes the enhanced coagulation mode of the present invention especially useful for concurrent cutting with coagulation, or for coagulation alone following an alternative cutting process that does not utilize the glow blade of the present invention. The wave shape 43 is an example of an "enhanced coagulation waveform" defined supra.

The variable wave shapes have an associated time-averaged output that may be varied from 50 to 500 volts (e.g., a sine wave with 100 volts RMS output voltage). Successful tissue cutting will occur, inter alia, with 100 volts while consuming only 5 watts of power, which implies a power range of 1.25 to 125 watts for the output voltage range of 50 to 500 volts. The lower output voltage of the RF generator 30, as compared the much higher output voltage of at least 1000 volts of a conventional electrosurgical device, results in lower current through the target tissue and bulk of the patient 9.

The power supply 31A comprises the glow oscillator 4 and glow amplifier 5, wherein the glow oscillator 4 drives the glow amplifier 5. The output of the glow amplifier 5 is a low-voltage, high-current signal to heat up the conductive element 507a of the glow blade 14. By adjusting the duty cycle of the glow oscillator 4, one can adjust the temperature of conductive element 507a. The glow components (i.e., the glow oscillator 4 and the glow amplifier 5) are like a variable battery connected across a light bulb. The glow oscillator 4 and glow amplifier 5 could be replaced by any suitable adjustable power source. In one embodiment, the power supply 31A is powered by a DC source (e.g., one or more batteries) that drives a pulse amplifier to generate a pulse train that is sent to the conductive element 507a. The power of the pulse train from the power supply 31A controls the temperature of the conductive element 507a. The power of the pulse train from the power supply 31A may be varied by adjustment of the pulse amplitude, duty cycle and/or the pulse rate. In one embodiment, the power source for the power supply 31A is an AC power source such as 115 VAC mains (e.g., the electrosurgical adapter 53A of FIG. 9, described infra).

The power supply 31B comprises the glow oscillator 12 and glow amplifier 13, wherein the glow oscillator 12 drives the glow amplifier 13. As stated supra, the conductive element 507b may be heated or non-heated when used for cutting and/or coagulation. When the conductive element 507b is heated, the output of the glow amplifier 13 is a low-voltage, high-current signal to heat up the conductive element 507b of the glow blade 14. By adjusting the duty cycle of the glow oscillator 4, one can adjust the temperature of conductive element 507b. The glow components (i.e., the glow oscillator 12 and the glow amplifier 13) are like a variable battery connected across a light bulb. The glow oscillator 12 and glow amplifier 13 could be replaced by any suitable adjustable power source. In one embodiment, the power supply 31B is a DC source (e.g., one or more batteries) that drives a pulse amplifier to generate a pulse train that is sent to the conductive element 507b. The power of the pulse train from the power supply 31B controls the temperature of the conductive element 507b, which controls the temperature of the conductive element 507b. The power of the pulse train from the power supply 31B may be varied by adjustment of the pulse amplitude, duty cycle and/or the pulse rate. In one embodiment, the power source for the power supply 31B is an AC power source such as 115 VAC mains (e.g., the electrosurgical adapter 53B of FIG. 9, described infra).

The RF generator 30 is electrically coupled to the power supplies 31A and 31B. The hot lead 8 of the high voltage amplifier 3 is electrically connected to the high side of the glow amplifier 5 as in FIG. 1 and also to the conductive element 507a. The low side of the high voltage amplifier 3 is electrically connected in FIG. 2 to an internal circuit ground 10A which is also electrically connected to the low side of the glow amplifier 13 and to conductive element 507b. Outputs of the glow amplifier 5 and the glow amplifier 13 are electrically connected to and across the resistive elements within conductive elements 507a and 507b of the dual glow blade 14 via cable 21 and 22, respectively. When the conductive elements 507a and 507b touch the patient 9, the tissue 32 of the patient 9 is cut by the extremities of the elements.

Figure 6:
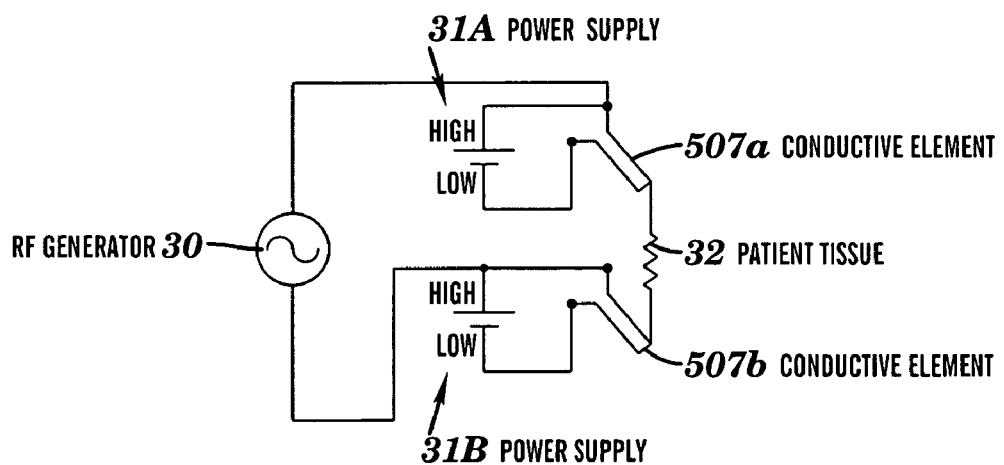
FIG. 6 depicts an equivalent electric circuit representing the electrosurgical apparatus and patient of FIG. 2, in accordance with embodiments of the present invention.

FIG. 6 depicts an equivalent electric circuit representing the electrosurgical apparatus and patient of FIG. 2, in accordance with embodiments of the present invention. In FIG. 6 the high side of the RF generator 30 is electrically connected to conductive element 507a. The low side or common of the RF generator 30 is electrically connected to conductive element 507b. The power supplies 31A and 31B are represented simplistically as batteries and heat the conductive elements but may alternatively be represented by AC power sources. The power supplies 31A and 31B heat up the conductive elements, while the RF generator 30 provides energy for tissue cutting. Those skilled in the art realize that the outputs of each respective supply 31A and 31B are reversible; i.e.; high can be swapped with low and vice versa.

The conductive elements 507a and 507b are in physically proximity and are separated by a gap that is equal to the minimum distance or separation between the conductive elements 507a and 507b. The range of gap size that may be beneficially used and depends on the nature of the surgery and the tissue being cut. The conductive elements 507a and 507b may have any functional geometry as discussed infra in conjunction with FIG. 4B. An exemplary but not limiting range of gap sizes is 0.010 inch to 1 inch.

Figure 4C:
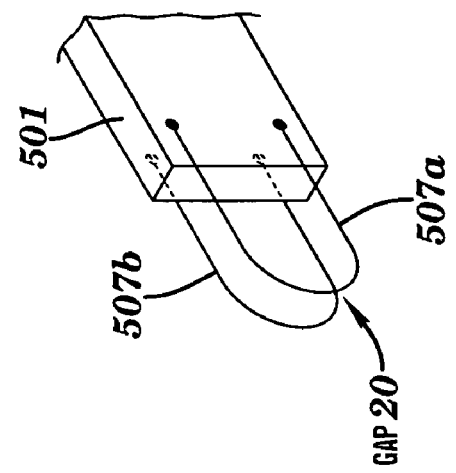
FIGS. 4A, 4B, and 4C depict conductive elements of the bipolar glow blade of FIG. 2 in various geometric configurations, in accordance with embodiments of the present invention.
Figure 4B:
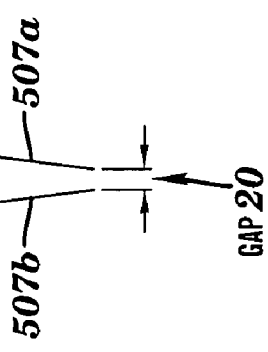
Figure 4A:
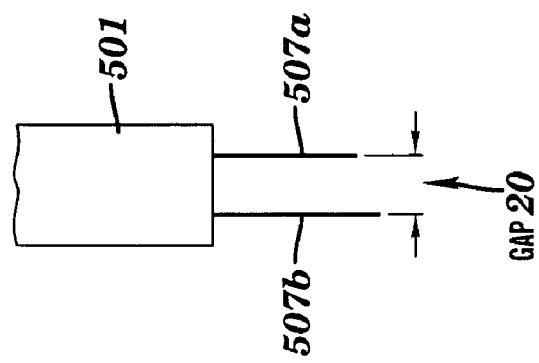

FIGS. 4A, 4B, and 4C depict conductive elements 507a and 507b of the bipolar glow blade 14 of FIG. 2 in various geometric configurations, in accordance with embodiments of the present invention. The size and shape of conductive elements 507a and 507b may vary depending on the type of surgical procedure and other factors such as durability and cost. The conductive elements 507a and 507b may exist in any functional geometry that is suitable for cutting and/or coagulating tissue. The conductive elements 507a and 507b depicted in FIGS. 4A, 4B, and 4C are merely illustrative and do not limit the scope of possible geometries for conductive elements 507a and 507b.

In FIG. 4A, conductive elements 507a and 507b are each linear elements which are parallel to each other as in FIG. 2. The conductive elements 507a and 507b are separated by gap 20. The conductive elements 507a and 507b may have equal or unequal lengths. For example, conductive element 507b is longer and thicker than conductive element 507a in FIG. 2. In one embodiment, the shorter conductive element 507a cuts and/or coagulates while the longer conductive element 507b is unheated.

In FIG. 4B, conductive elements 507a and 507b are each linear elements which form an acute angle with respect to each other to each other. The conductive elements 507a and 507b are separated by gap 20. In one embodiment the conductive elements 507a and 507b may be projected to intersect in a point. The conductive elements 507a and 507b may have equal or unequal lengths. For example, conductive element 507b may be longer than conductive element 507a. In one embodiment, the shorter conductive element 507a cuts and/or coagulates while the shorter conductive element 507b is unheated. The conductive elements 507a and 507b may be coplanar or may alternatively be non-coplanar.

In FIG. 4C, conductive elements 507a and 507b are loops which may be parallel or non-parallel to each other or co-linear or co-planar. The conductive elements 507a and 507b are separated by gap 20.

FIG. 9 depicts an alternative electrosurgical apparatus configured for bipolar operation with a bipolar glow blade for use with a patient, in accordance with embodiments of the present invention. The electrosurgical apparatus of FIG. 9 differs from the electrosurgical apparatus of FIGS. 2 and 6 in that: a commercial electrosurgical unit 50 of FIG. 9 replaces the RF generator 30 of FIGS. 2 and 6; and the electrosurgical adapters 53A and 53B of FIG. 9 replace the power supplies 31A and 31B, respectively, of FIGS. 2 and 6. In all other respects, the electrosurgical apparatus of FIG. 9 and the electrosurgical apparatus of FIGS. 2 and 6 are essentially the same electrosurgical apparatus with respect to structure and functionality.

The commercial electrosurgical unit 50 is the RF power portion of a conventional electrosurgical apparatus used in the prior art. The bipolar glow blade 14 (see FIG. 2) comprises the conductive elements 507a and 507b and operates in conjunction with the electrosurgical adapters 53A and 53B. The commercial electrosurgical unit 50 receives AC power as shown and has a high voltage output 51 and a common output 52. The high voltage output 51 is electrically connected, via the electrosurgical adapter 53A, to conductive element 507a which contacts the patient tissue 32. The common output 52 is electrically connected, via the electrosurgical adapter 53B to conductive element 507b, or alternatively conductive element 507b is non-heated, such that conductive element 507b contacts the patient tissue 32.

The electrosurgical adapter 53A, which converts AC power to a pulse train to provide power to the conductive element 507a, comprises a pulse generator/amplifier 56A and an RF isolation transformer 55A. An operator power control 54A connects to the pulse generator/amplifier 56A and controls the power in the pulse train by varying pulse rate, duty cycle, or amplitude of the pulse train, which controls the temperature of the conductive element 507a. The RF isolation transformer 55A allows power to be coupled from the pulse amplifier 56A to the conductive element 507a while providing a high impedance for any stray RF current flowing from the electrosurgical unit 50. The transformer 55A is wound with sufficient distance between primary and secondary coils to achieve the desired RF isolation and deliver the required power to be supplied to the conductive element 507a. In one embodiment, the electrosurgical adapter 53A may be replaced by a battery such as a battery representing the power supply 31A of FIGS. 2 and 6, for use with the commercial electrosurgical unit 50. Power to the conductive element 507a is supplied via the secondary of the isolation transformer 55A.

The electrosurgical adapter 53B, which converts AC power to a pulse train to provide power to the conductive element 507b, comprises a pulse generator/amplifier 56B and an RF isolation transformer 55B. An operator power control 54B connects to the pulse generator/amplifier 56B and controls the power in the pulse train by varying pulse rate, duty cycle, or amplitude of the pulse train, which controls the temperature of the conductive element 507b. The RF isolation transformer 55B allows power to be coupled from the pulse amplifier 56B to the conductive element 507b while providing a high impedance for any stray RF current flowing from the electrosurgical unit 50. The transformer 55B is wound with sufficient distance between primary and secondary coils to achieve the desired RF isolation and deliver the required power to be supplied to the conductive element 507b. In one embodiment, the electrosurgical adapter 53B may be replaced by a battery such as a battery representing the power supply 31A of FIGS. 2 and 6, for use with the commercial electrosurgical unit 50. Power to the conductive element 507b is supplied via the secondary of the isolation transformer 55B.

The output from the electrosurgical adapters 53A and 53B of FIG. 9 is analogous to the output from the power supplies 31A and 31B, respectively, of FIG. 2. In FIG. 2, the output of the power supplies 31A and 31B are electrically decoupled from the AC power source of the RF generator 30 (e.g., by use of a battery as a power source of the power supplies 31A and 31B), which prevents unwanted RF power from flowing from the RF generator 30 to the power source of the power supply 31. Similarly in FIG. 8, the output of the electrosurgical adapter 53 is electrically decoupled from its AC power source and hence the power source of the electrosurgical unit 50 due to the output of the electrosurgical adapter 53 being decoupled from by the RF isolation transformer 55, which prevents unwanted RF power from flowing from the electrosurgical adapter 53 to the power source of the electrosurgical adapter 53.

The bipolar glow blade may be used for rapid coagulation of tissue (without accompanying cutting of tissue) in order to stop bleeding immediately (e.g.; to stops uncontrolled bleeding of soldiers wounded in combat). In one embodiment for such coagulation applications, the conductive elements 507a and 507b may be brushed along the surface of the tissue being coagulated (e.g., moved in a brushing-type motion in a direction that is about parallel to the surface of the tissue being coagulated, with actual contact or with a small gap; e.g., about in the direction 62 in FIG. 2). In one embodiment, successful coagulation of tissue (without accompanying cutting of tissue) will occur with output power from the RF generator in a range of 1.25 to 125 watts.

Thus the RF generator 30 and the power supplies 31A and 31B are configured to operate concurrently, while the conductive elements 507a and 507b (or conductive element 507a only) are heated to a glow, to supply both sufficient RF power and associated electrical current across the living tissue 32 for cutting and/or coagulating the living tissue 32 by the conductive elements 507a and 507b.

The inventor of the present invention has determined that the bipolar glow blade embodiment of the present invention may be beneficially employed in a non-glowing mode for the conductive elements, as an improvement over conventional electrosurgical devices of the prior art, if the dual glow blade embodiment is implemented as described supra except that the conductive elements 507a and 507b perform cutting and/or coagulation of tissue at a temperature below the minimum glow temperature of the material of the conductive elements (e.g., at a temperature in a range of about 300° F. to just below the minimum glow temperature). The minimum glow temperature of the material is defined as the minimum temperature at which the material glows (i.e., emits electromagnetic radiation in the visible portion of the electromagnetic spectrum).

Figure 10:
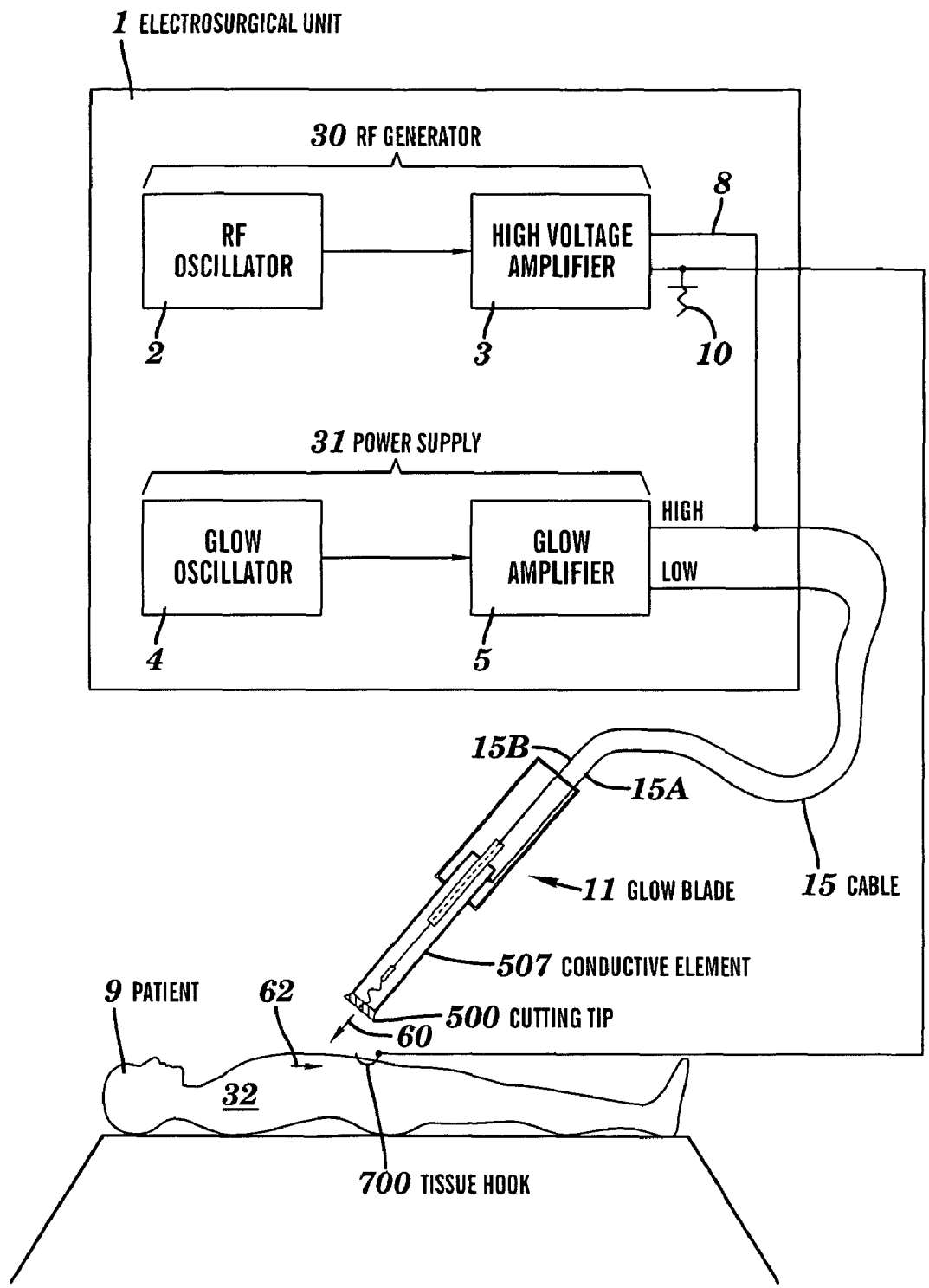
FIG. 10 depicts a proxipolar mode of electrosurgical cutting, in accordance with embodiments of the present invention.

FIG. 10 depicts a proxipolar mode of electrosurgical cutting, in accordance with embodiments of the present invention. The proxipolar mode of cutting and coagulation has features of both monopolar and bipolar with respect to RF return connection positions on the patient 9. FIG. 10 is similar to FIG. 1 except that a tissue hook 700 replaces the patient pad 7 of FIG. 1 as an electrically conducting element for the RF return path back to circuit ground 10. In one embodiment, the tissue hook 700 is located proximate to where the tissue is being cut and/or coagulated by conductive element 507 (i.e., from 0.1 inches to 12 inches from where the tissue is being cut and/or coagulated as measured along the exterior surface of the tissue). In one embodiment, the tissue hook 700 is located remote from where the tissue is being cut and/or coagulated by conductive element 507 (i.e., greater than 12 inches from where the tissue is being cut and/or coagulated as measured along the exterior surface of the tissue). In one embodiment, the tissue hook 700 resembles a fishhook without a barb. Generally, the tissue hook 700 is an electrically conducting element that can be fastened to the tissue 32 to prevent relative motion between the tissue hook 700 at a location in the tissue 32 where the tissue hook 700 is fastened to the tissue 32 and may puncture or clamp the tissue 32. This could be as close as 1 inch to the incision, depending on characteristics of the tissue 32 and requirements of the surgery. The tissue hook 700 can be employed in lieu of a patient pad 7, because the heated blade technology consumes a compatibly lower power, and a smaller surface area of patient tissue contact is adequate for RF return. In one embodiment, for incisions at low power (e.g., 5 to 15 watts), the conductive element 507 may be employed in the proxipolar mode as an unheated cutting element. Since the tissue hook 700 may have any geometric shape that enables the tissue hook 700 to be fastened to the tissue 32, the tissue hook 700 could take numerous forms, such as a hook, clip, clamp, needle, or other tissue contact means. An advantage of using the tissue hook 700 instead of the patient pad 7 is that the RF current in the patient 9 flows primarily from the conductive element 507 to the tissue hook 700. Essentially no currents flow through sensitive tissue elsewhere in the patient 9.

Figure 11:
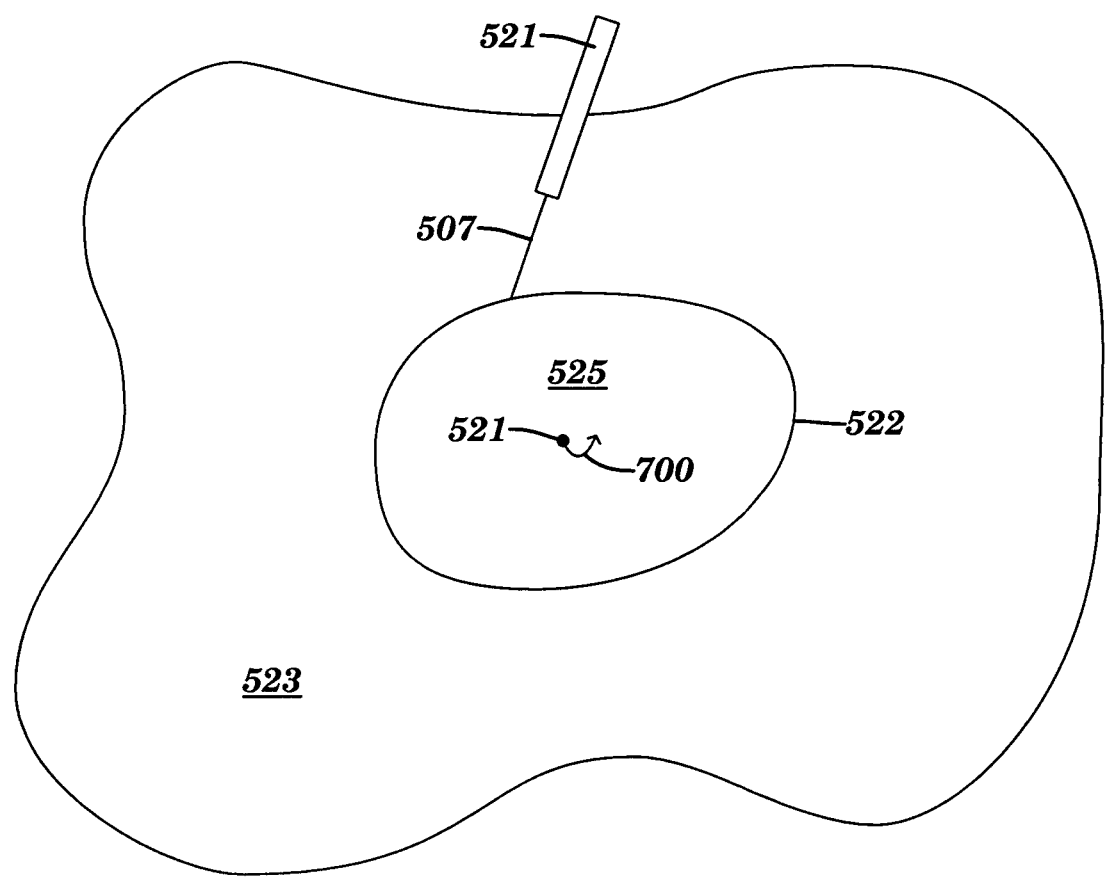
FIG. 11 depicts a circumpolar operational mode for tumor removal, in accordance with embodiments of the present invention.

FIG. 11 depicts a circumpolar operational mode for tumor removal, in accordance with embodiments of the present invention. The circumpolar mode for tumor removal is an application of the proxipolar mode, wherein the tissue hook 700 is placed in the tissue of a tumor 525 targeted for excision. The tumor 525 is disposed within tissue 523. In one embodiment, the tissue hook 700 is placed about in the center 521 of the tumor 525 or in other tissue being excised. The conductive element 507 circumscribes a path 522 around the tumor 525 as the conductive element 507 excises the tumor 525. In the circumpolar mode, the RF current flowing through the tissue flows primarily from the conductive element 507 through the tumor 525 to the tissue hook 700, which eliminates unwanted currents flowing, for example, through sensitive brain tissue located near a brain tumor when surgically removing such tumor.

Alternative Energy Sources

Figure 12:
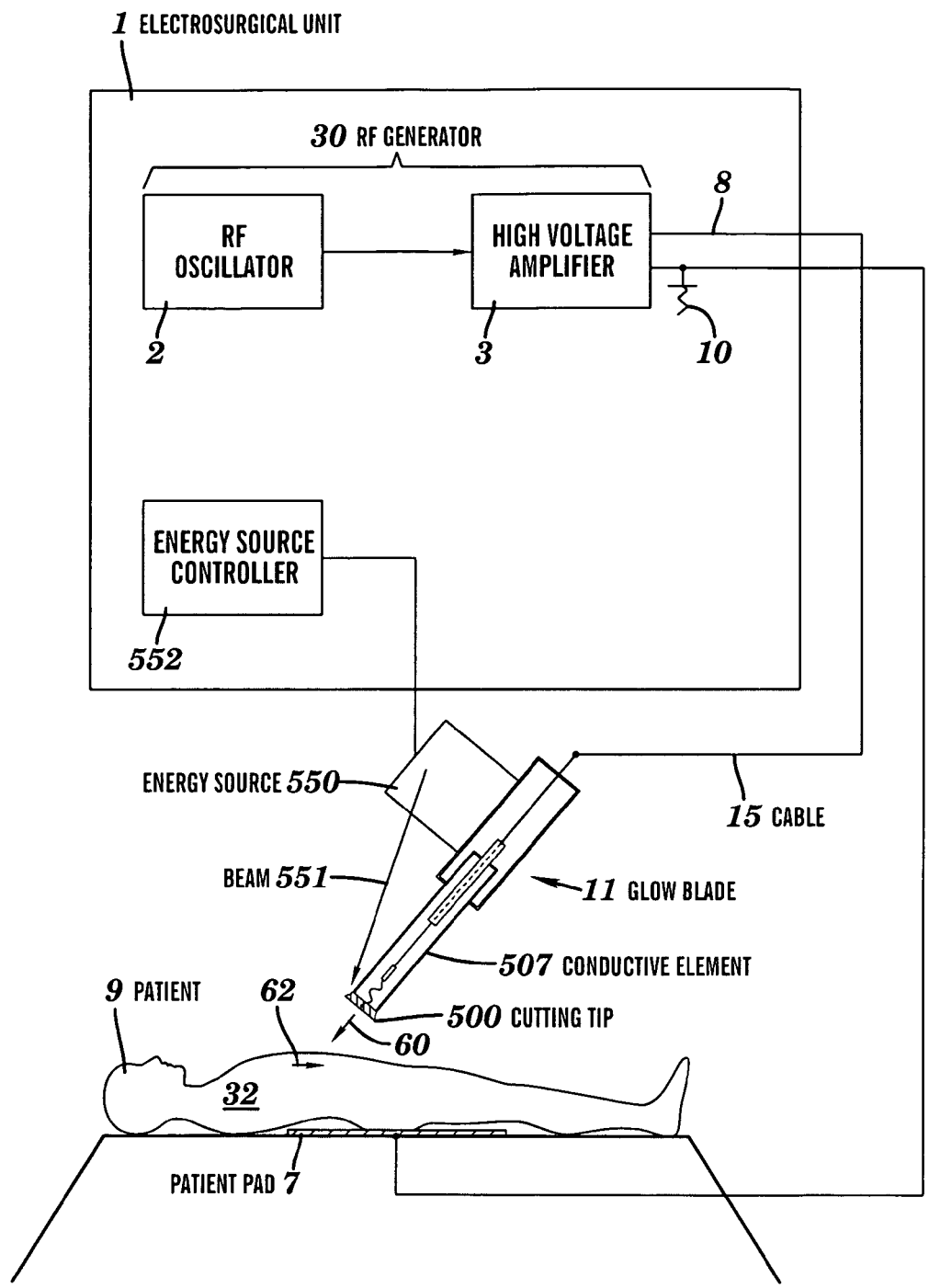
FIG. 12 depicts the electrosurgical apparatus in the monopolar mode of FIG. 1 with the power supply being replaced by an alternative heating source, in accordance with embodiments of the present invention.
Figure 13:
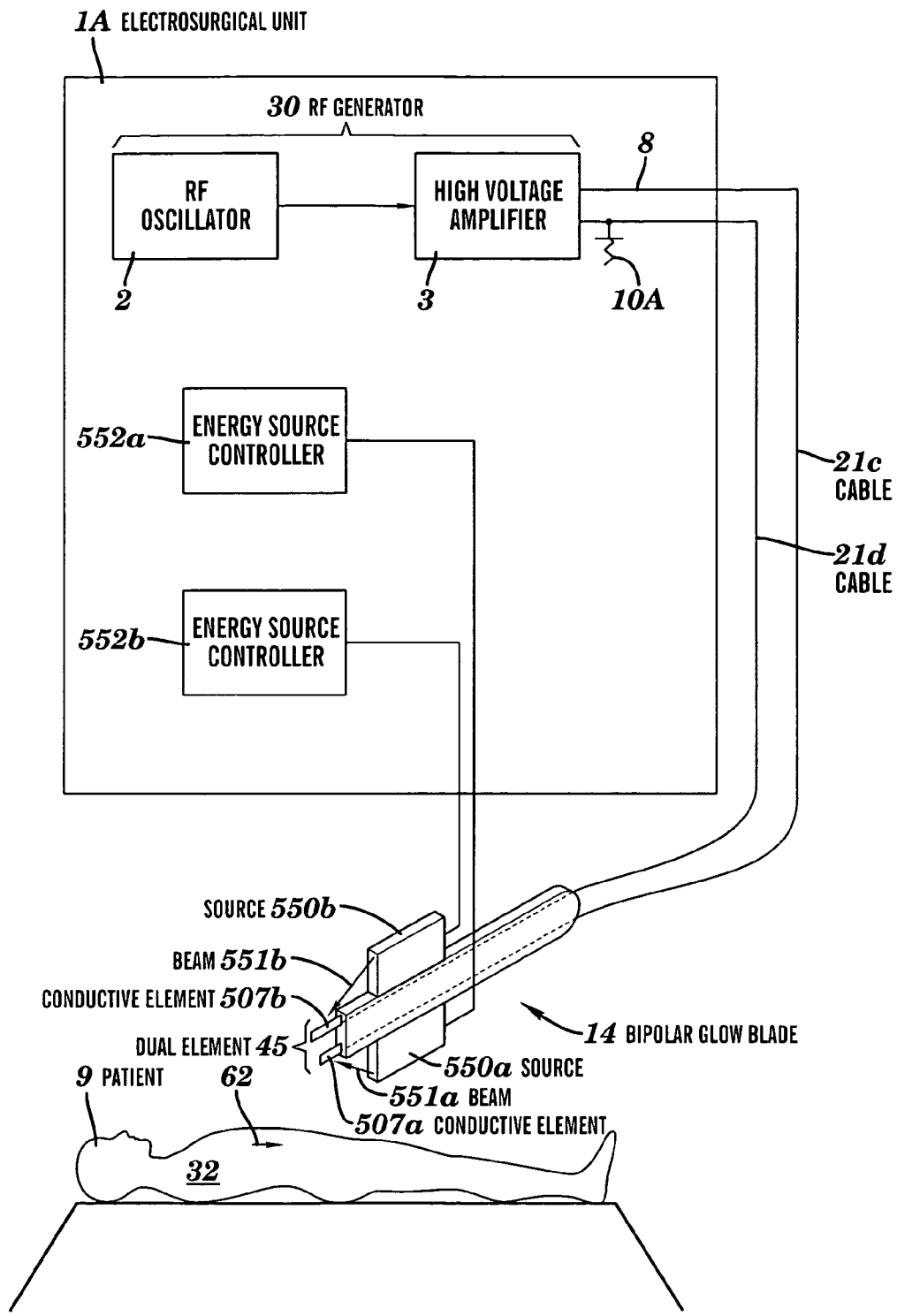
FIG. 13 depicts the electrosurgical apparatus in the bipolar mode of FIG. 2 with the power supplies being replaced by alternative heating sources, in accordance with embodiments of the present invention.

While the preceding description of the present invention has described heating the glow blade electrically, the glow blade may alternatively be heated by other heating mechanisms using alternative energy sources (e.g., laser heating, ultrasonic heating, flame heating, plasma heating, etc.) in a glowing mode or a non-glowing mode to implement the embodiments described herein for cutting and/or coagulating living tissue of a mammal. The scope of the present invention includes any method of using a heated glow blade to cut and/or coagulate living tissue of a mammal, regardless of the method by which the glow blade is heated. FIGS. 12 and 13 illustrate infra alternative energy sources for heating the glow blade of the present invention.

FIG. 12 depicts the electrosurgical apparatus in the monopolar mode of FIG. 1 with the power supply 31 being replaced by an alternative heating source, namely an energy source 550 and accompanying energy source controller 552, in accordance with embodiments of the present invention. The energy source 550 is controlled by the energy source controller 552. The conductor cable 15 electrically couples the RF generator to the glow blade 11. In one embodiment, the energy source 550 comprises any energy source configured to focus an energy beam 551 on the cutting tip 500 with sufficient energy to heat the cutting tip 500 to a glow or to a non-glowing temperature sufficient for cutting and/or coagulating tissue of the patient 9. The energy source 550 is mechanically affixed to the glow blade 11 (e.g., at the metal tubing 501 or the non-metallic handle 16 shown in FIG. 3) in manner that constrains the energy beam 551 to point toward the cutting tip 500 continuously while the glow blade is being moved. In one embodiment, the energy source 550 is a source of laser radiation whose wavelength and power are configured to sufficiently heat the cutting tip 500 to for cutting and/or coagulating tissue of the patient 9. In one embodiment, the energy source 550 is a source of sonic radiation whose frequency and power are configured to sufficiently heat the cutting tip 500 to for cutting and/or coagulating tissue of the patient 9. In one embodiment, the energy source 550 provides flame radiation configured to sufficiently heat the cutting tip 500 for cutting and/or coagulating tissue of the patient 9. In one embodiment, the energy source 550 provides plasma configured to sufficiently heat the cutting tip 500 for cutting and/or coagulating tissue of the patient 9. The energy source 550 generally represents any energy source coupled to the glow blade 11 (e.g., mechanically affixed to the glow blade) that can provide energy to the cutting tip 500, said provided energy being of sufficient magnitude to heat the cutting tip 500 to a glow or to a non-glowing temperature sufficient for cutting and/or coagulating tissue of the patient 9 by the glow blade 11 in accordance with the present invention as described supra.

FIG. 13 depicts the electrosurgical apparatus in the bipolar mode of FIG. 2 with the power supplies 31A and 31B being replaced by an alternative heating sources, namely energy sources 550a and 550b along with accompanying energy source controllers 552a and 552b, in accordance with embodiments of the present invention. The energy sources 550a and 550b are controlled by the energy source controllers 552a and 552b, respectively. The conductor cables 21c and 21d electrically couple the RF generator 30 to the bipolar glow blade 14. In one embodiment, the energy sources 550a and 550b comprises any energy source configured to focus energy beams 551a and 551b on the conductive elements 507a and 507b with sufficient energy to heat the conductive elements 507a and 507b to a glow or to a non-glowing temperature sufficient for cutting and/or coagulating tissue of the patient 9. The energy sources 550a and 550b are mechanically affixed to the glow blade 14 (e.g., at the metal tubing or non-metallic handle similar to the metal tubing 501 or the non-metallic handle 16 shown in FIG. 3 for the glow bale 11) in manner that constrains the energy beams 551a and 551b to point toward conductive elements 507a and 507b continuously while the glow blade is being moved. In one embodiment, the sources 550a and 550b are sources of laser radiation whose wavelength and power are sufficiently configured to heat the conductive elements 507a and 507b, respectively, for cutting and/or coagulating tissue of the patient 9. In one embodiment, the energy sources 550a and 550b are ultrasound sources of sonic radiation whose frequency and power are sufficiently configured to heat the conductive elements 507a and 507b, respectively, for cutting and/or coagulating tissue of the patient 9. In one embodiment, the energy sources 550a and 550b provide flame radiation configured to sufficiently heat the conductive elements 507a and 507b for cutting and/or coagulating tissue of the patient 9. In one embodiment, the energy sources 550a and 550b provide plasma configured to sufficiently heat the conductive elements 507a and 507b for cutting and/or coagulating tissue of the patient 9. In one embodiment only one energy source is employed to heat one conductive element while the second conductive element is unheated. The energy sources 550a and 550b generally represents any energy sources coupled to the glow blade 14 (e.g., mechanically affixed to the glow blade) that can provide energy to conductive elements 507a and 507, said provided energy being of sufficient magnitude to heat the conductive elements 507a and 507b to a glow or to a non-glowing temperature sufficient for cutting and/or coagulating tissue of the patient 9 by the glow blade 14 in accordance with the present invention as described supra.

EXAMPLE

The electrosurgical apparatus of the present invention is fully operational. In one embodiment, the conductive elements are constructed with an outer member of stainless steel tubing. Internal to the tubing is a heated nickel chrome resistance wire. Both the monopolar and bipolar glow blades have been used successfully to cut and coagulate live pig tissue. A conventional electrosurgical generator was set up in an enhanced coagulation mode, crest factor equal to 8, and was employed in conjunction with the electrosurgical adapter of the present invention to cut and coagulate live pig liver using a glow blade. When cutting, the single glow blade was moved across the target tissue similar to using a conventional knife. In practice, however, some back and forth motion may be employed. In one embodiment, the element may be placed over the tissue and its edge gently pressed against and into the tissue to create a cut.

It is also possible to undercut; i.e., to move the glow blade under the target tissue, where the blade may be shaped as required to first penetrate the target tissue, followed by cutting under the target tissue. Cutting along a curve is practical, since the glow blade may be easily bent by a user (e.g., a surgeon) to the required curvature.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. An electrosurgical apparatus for cutting and/or coagulating a local portion of living tissue of a mammal, said apparatus comprising:
   A cutting probe; and
   a radio frequency (RF) generator such that a first output of the RF generator is electrically connected to the cutting probe;
   wherein the RF generator is configured to supply sufficient RF power and associated electrical current across the living tissue for performing said cutting and/or coagulating by the cutting probe while sufficient energy is being supplied to heat the cutting probe to a sufficient temperature to facilitate the transport of RF energy to target tissue for performing said cutting and/or coagulating by the cutting probe.

2. The electrosurgical apparatus of claim 1, wherein said sufficient RF power and associated electrical current across the living tissue are being supplied by the RF generator concurrent with said sufficient energy being supplied to the cutting probe to heat the cutting probe to said sufficient temperature.

3. The electrosurgical apparatus of claim 2, wherein the cutting probe comprises a single conductive element that glows at said sufficient temperature, and wherein said sufficient energy is being supplied to the cutting probe to heat the single conductive element to said sufficient temperature for performing said cutting and/or coagulating while the single conductive element is glowing.

4. The electrosurgical apparatus of claim 2, wherein the cutting probe comprises a single conductive element that does not glow at said sufficient temperature, and wherein said sufficient energy is being supplied to the cutting probe to heat the single conductive element to said sufficient temperature for performing said cutting and/or coagulating while the single conductive element is not glowing.

5. The electrosurgical apparatus of claim 2, wherein the cutting probe comprises a first conductive element and a second conductive element, wherein the first conductive element and the second conductive element each glow at said sufficient temperature, and wherein said sufficient energy is being supplied to the first conductive element and the second conductive element to heat the first conductive element and the second conductive element to said sufficient temperature for performing said cutting and/or coagulating while the first conductive element and the second conductive element are glowing.

6. The electrosurgical apparatus of claim 2, wherein the cutting probe comprises a first conductive element and a second conductive element, wherein the first conductive element glows at said sufficient temperature, and wherein said sufficient energy is being supplied to the first conductive element to heat the first conductive element to said sufficient temperature for performing said cutting and/or coagulating while the first conductive element is glowing and the second conductive element is not heated.

7. The electrosurgical apparatus of claim 2, wherein the cutting probe comprises a first conductive element and a second conductive element, wherein the first conductive element does not glow at said sufficient temperature, and wherein said sufficient energy is being supplied to the first conductive element to heat the first conductive element to said sufficient temperature for performing said cutting and/or coagulating while the first conductive element is heated but not glowing and the second conductive element is not heated.

8. The electrosurgical apparatus of claim 2, wherein the cutting probe comprises a first conductive element and a second conductive element;
   wherein the electrosurgical apparatus is configured to flow said electric current across the living tissue disposed between the first conductive element and the second conductive element.

9. The electrosurgical apparatus of claim 1,
   wherein the electrosurgical apparatus further comprises an energy source for heating the cutting probe in addition to the RF generator.

10. The electrosurgical apparatus of claim 9, wherein the energy source supplies electrical energy.

11. The electrosurgical apparatus of claim 9, wherein the energy source comprises a source of laser radiation.

12. The electrosurgical apparatus of claim 1, wherein the cutting probe contains nickel.

13. A method for cutting and/or coagulating a local portion of living tissue of a mammal, said method comprising cutting and/or coagulating the local portion of the living tissue of a mammal with a cutting probe accompanied by sufficient electrical current across the living tissue to enable said cutting and/or coagulating to be performed while the cutting probe is heated to a sufficient temperature, the method further comprising heating the cutting probe to the sufficient temperature to facilitate the transport of RF energy to target tissue.

14. The method of claim 13,
wherein said cutting and/or coagulating comprises using an electrosurgical apparatus for performing said cutting and/or coagulating,
wherein the electrosurgical apparatus comprises the cutting probe, a radio frequency (RF) generator such that a first output of the RF generator is electrically connected to the cutting probe, and an energy source coupled to the cutting probe, and
wherein said using the electrosurgical apparatus for performing said cutting and/or coagulating comprises said RF generator supplying sufficient RF power and associated electrical current across the living tissue for performing said cutting and/or coagulating by the cutting probe and said energy source supplying sufficient energy to heat the cutting probe to a sufficient temperature for performing said cutting and/or coagulating by the cutting probe, said supplying sufficient RF power and said supplying sufficient energy being concurrently performed.

15. The method of claim 14, wherein the cutting probe comprises a single conductive element that is glowing at said sufficient temperature while said cutting and/or coagulating is being performed.

16. The method of claim 14, wherein the cutting probe comprises a single conductive element that is not glowing at said sufficient temperature while said cutting and/or coagulating is being performed.

17. The method of claim 14, wherein the cutting probe comprises a first conductive element and a second conductive element, wherein the first conductive element and the second conductive element are both glowing at said sufficient temperature while said cutting and/or coagulating is being performed.

18. The method of claim 14, wherein the cutting probe comprises a first conductive element and a second conductive element, wherein the first conductive element is heated at said sufficient temperature and the second conductive element is not heated while said cutting and/or coagulating is being performed.

19. The method of claim 14, wherein the energy source comprises a source of laser radiation.

20. The method of claim 14, wherein said cutting and/or coagulating consists of said cutting and said coagulating, wherein said cutting and said coagulating are performed concurrently, and wherein the first output of the RF generator is an enhanced coagulation waveform having a duty cycle from about 2% to about 20% and/or having a crest factor from about 5 to about 10.

21. The method of claim 13, wherein the cutting probe comprises a single conductive element, and wherein a second output of an RF generator is electrically connected to an electrically conducting element that is in direct physical and electrical contact with the mammal to facilitate electric current across the living tissue between the single conductive element and the electrically conducting element.

22. The method of claim 21, wherein the second output of the RF generator is electrically connected to the electrically conducting element and is positioned in the living tissue proximate to a local portion where the living tissue is being cut and/or coagulated by the single conductive element.

23. The method of claim 22, wherein the local portion of the living tissue comprises a tumor, wherein said cutting and/or coagulating comprises excising the tumor by the single conductive element, and wherein the second output of the RF generator is electrically connected to the electrically conducting element which is positioned in the local portion of the living tissue of the tumor being excised.

24. The method of claim 13, wherein the heating the cutting probe to the sufficient temperature is performed with electrical energy.

25. The method of claim 13, wherein the cutting probe contains nickel.

26. An electrosurgical apparatus for cutting and/or coagulating a local portion of living tissue of a mammal, said apparatus comprising:
A cutting probe; and
a radio frequency (RF) generator such that a first output of the RF generator is electrically connected to the cutting probe;
wherein the RF generator is configured to supply sufficient RF power and associated electrical current across the living tissue for performing said cutting and/or coagulating by the cutting probe while sufficient energy is being supplied to heat the cutting probe to at least 300 degrees Fahrenheit.

* * * * *